(12) United States Patent
Chen et al.

(10) Patent No.: US 11,714,065 B2
(45) Date of Patent: Aug. 1, 2023

(54) METHOD OF MEASURING HEMATOCRIT AND METHOD OF TESTING BLOOD

(71) Applicant: Industrial Technology Research Institute, Hsinchu (TW)

(72) Inventors: Chu-Hsuan Chen, Hsinchu County (TW); Yu-Fang Yen, Hsinchu (TW); Yi-Ting Tung, Tainan (TW); Fen-Fei Lin, Hsinchu County (TW); Yi-Yun Yuan, Hsinchu County (TW); Wen-Pin Hsieh, Miaoli County (TW)

(73) Assignee: Industrial Technology Research Institute, Hsinchu (TW)

( * ) Notice: Subject to any disclaimer, the term of this patent is extended or adjusted under 35 U.S.C. 154(b) by 395 days.

(21) Appl. No.: 17/013,658

(22) Filed: Sep. 7, 2020

(65) Prior Publication Data
US 2020/0400612 A1    Dec. 24, 2020

Related U.S. Application Data

(62) Division of application No. 15/791,415, filed on Oct. 24, 2017, now abandoned.
(Continued)

(30) Foreign Application Priority Data

Oct. 17, 2017   (TW) .................................. 106135409

(51) Int. Cl.
*G01N 27/48* (2006.01)
*G01N 27/02* (2006.01)
(Continued)

(52) U.S. Cl.
CPC ............. *G01N 27/48* (2013.01); *G01N 27/02* (2013.01); *G01N 27/3274* (2013.01);
(Continued)

(58) Field of Classification Search
CPC ........ G01N 33/49; G01N 33/80; G01N 33/26; G01N 33/48785; G01N 27/3274;
(Continued)

(56) References Cited

U.S. PATENT DOCUMENTS

| 2007/0235346 A1* | 10/2007 | Popovich | ............... C12Q 1/004 204/403.01 |
| 2008/0000780 A1* | 1/2008 | Tonks | ................ G01N 27/3274 205/792 |
| 2016/0290987 A1* | 10/2016 | Saeda | .............. G01N 33/48707 |

OTHER PUBLICATIONS

"Office Action of Europe Counterpart Application", dated Nov. 30, 2021, pp. 1-6.

* cited by examiner

*Primary Examiner* — Gurpreet Kaur
(74) *Attorney, Agent, or Firm* — JCIPRNET

(57) ABSTRACT

A method of measuring hematocrit is provided. The method for measuring hematocrit includes the following steps. A test strip is provided. The test strip includes a reaction region and a pair of electrodes disposed in the reaction region. A whole blood sample is entered to the reaction region. After the whole blood sample enters the reaction region, a plurality of sets of square wave voltages are intermittently applied to the pair of electrodes based on a square wave voltammetry method to obtain a plurality of feedbacks related to hematocrit. An interval between two adjacent sets of square wave voltages ranges from 0.1 seconds to 4 seconds. A feedback of an n-th set of square wave voltages is obtained to calculate a hematocrit value of the whole blood sample and n is a positive integer greater than 1. A hematocrit value is calculated according to the feedback.

7 Claims, 7 Drawing Sheets

Related U.S. Application Data

(60) Provisional application No. 62/413,449, filed on Oct. 27, 2016.

(51) Int. Cl.
*G01N 27/327* (2006.01)
*G01N 27/42* (2006.01)
*G01N 33/487* (2006.01)
*G01N 33/49* (2006.01)
*G01R 27/22* (2006.01)

(52) U.S. Cl.
CPC ....... *G01N 27/42* (2013.01); *G01N 33/48785* (2013.01); *G01N 33/49* (2013.01); *G01R 27/22* (2013.01)

(58) Field of Classification Search
CPC ........ G01N 27/48; G01N 27/27; G01N 27/02; A61B 5/14535
See application file for complete search history.

METHOD OF MEASURING HEMATOCRIT AND METHOD OF TESTING BLOOD

CROSS-REFERENCE TO RELATED APPLICATION

This application is a divisional application of and claims the priority benefit of U.S. application Ser. No. 15/791,415, filed on Oct. 24, 2017, which claims the priority benefits of U.S. provisional application Ser. No. 62/413,449, filed on Oct. 27, 2016 and Taiwan application Ser. No. 106135409, filed on Oct. 17, 2017. The entirety of each of the above-mentioned patent applications is hereby incorporated by reference herein and made a part of this specification.

TECHNICAL FIELD

The disclosure relates to a method of measuring hematocrit and a method of testing blood, and particularly relates to a method of measuring of hematocrit of a whole blood sample and a method of testing blood.

BACKGROUND

Hematocrit (Hct) mainly refers to the proportion of blood cells (mostly red blood cells) in the whole blood, which has been added with an anticoagulant and sendimented by centrifugation. Blood testing apparatuses in clinical laboratories generally use blood plasma as test samples. In other words, the test is carried out on blood plasma obtained through a centrifugation process of blood. Hence, the variation of Hct among test samples does not affect the test results.

However, in blood testing apparatuses for point-of-care testing (POCT) or over-the-counter (OTC) testing, whole blood samples are often used directly for measurement in order to reduce time and cost required for testing. In other words, Hct which differs from one individual to another may result in a test error. Besides, the temperature and the humidity at which the test sample is preserved or the temperature and the humidity at which the testing apparatuses are operated also affect testing results on Hct.

SUMMARY

One or some embodiments of the disclosure provide a method of measuring hematocrit, and the method includes the following steps. A test strip is provided. The test strip includes a reaction region and a pair of electrodes disposed in the reaction region. A whole blood sample is entered into the reaction region. After the whole blood sample enters the reaction region, a set of square wave voltages is applied to the pair of electrodes based on a square wave voltammetry method to obtain a feedback related to hematocrit. An interval between an initial time when the whole blood sample enters the reaction region and an initial time when the set of square wave voltages is applied ranges from 0.1 seconds to 200 seconds. A hematocrit value is calculated according to the feedback.

One or some embodiments of the disclosure provide a method of testing blood, and the method includes the following steps. A test strip is provided. The test strip includes a first reaction region, a pair of first electrodes disposed in the first reaction region, a second reaction region, and a pair of second electrodes disposed in the second reaction region. A whole blood sample is entered into the first reaction region and the second reaction region. Two sets of square wave voltages are applied to the pair of first electrodes based on a square wave voltammetry method after the whole blood sample enters the first reaction region, so as to respectively obtain a first feedback and a second feedback related to hematocrit; A voltage is applied to the pair of second electrodes to obtain a third feedback and thereby calculate a concentration of a target analyte in the whole blood sample. Whether a ratio of the first feedback with respect to the second feedback falls within a predetermined range is determined. The concentration of the target analyte is adopted if the ratio of the first feedback with respect to the second feedback falls within the predetermined range, and a message of anomalous testing is provided if the ratio of the first feedback with respect to the second feedback does not fall within the predetermined range.

One or some embodiments of the disclosure provide a method of measuring hematocrit, and the method includes the following steps. A test strip is provided. The test strip includes a reaction region and a pair of electrodes disposed in the reaction region. A whole blood sample is entered into the reaction region. A plurality of sets of square wave voltages are continuously applied to the pair of electrodes based on a square wave voltammetry method to obtain a plurality of feedbacks related to hematocrit. An interval between two adjacent sets of square wave voltages ranges from 0.1 seconds to 4 seconds. A feedback of an n-th set of square wave voltages is obtained to calculate a hematocrit value of the whole blood sample. Here, n is a positive integer greater than 1.

One or some embodiments of the disclosure provide a method of testing blood, and the method includes the following steps. A test strip is provided. The test strip includes a first reaction region, a pair of first electrodes disposed in the first reaction region, a second reaction region, and a pair of second electrodes disposed in the second reaction region. A whole blood sample is entered into the first reaction region and the second reaction region. A plurality of sets of square wave voltages are continuously applied to the pair of first electrodes based on a square wave voltammetry method to obtain a plurality of feedbacks related to hematocrit. A voltage is applied to the pair of second electrodes to calculate a concentration of a target analyte in the whole blood sample. Whether a ratio of the two arbitrary feedbacks of the square wave voltages after the first set falls within a predetermined range is determined. The concentration of the target analyte is adopted if the ratio of the two arbitrary feedbacks of the square wave voltages after the first set falls within the predetermined range, and a message of anomalous testing is provided if the ratio of the two arbitrary feedbacks of the square wave voltages after the first set does not fall within the predetermined range.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1A:
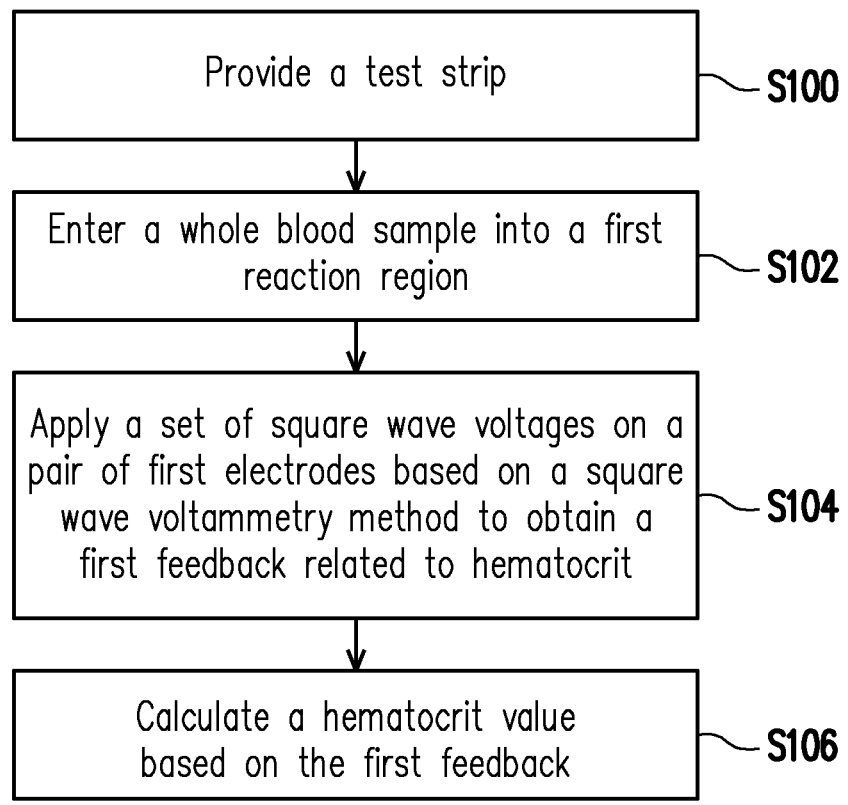
FIGS. 1A and 1B are respectively flowcharts illustrating a method of measuring hematocrit and a method of testing blood according to an embodiment of the disclosure.
Figure 1B:
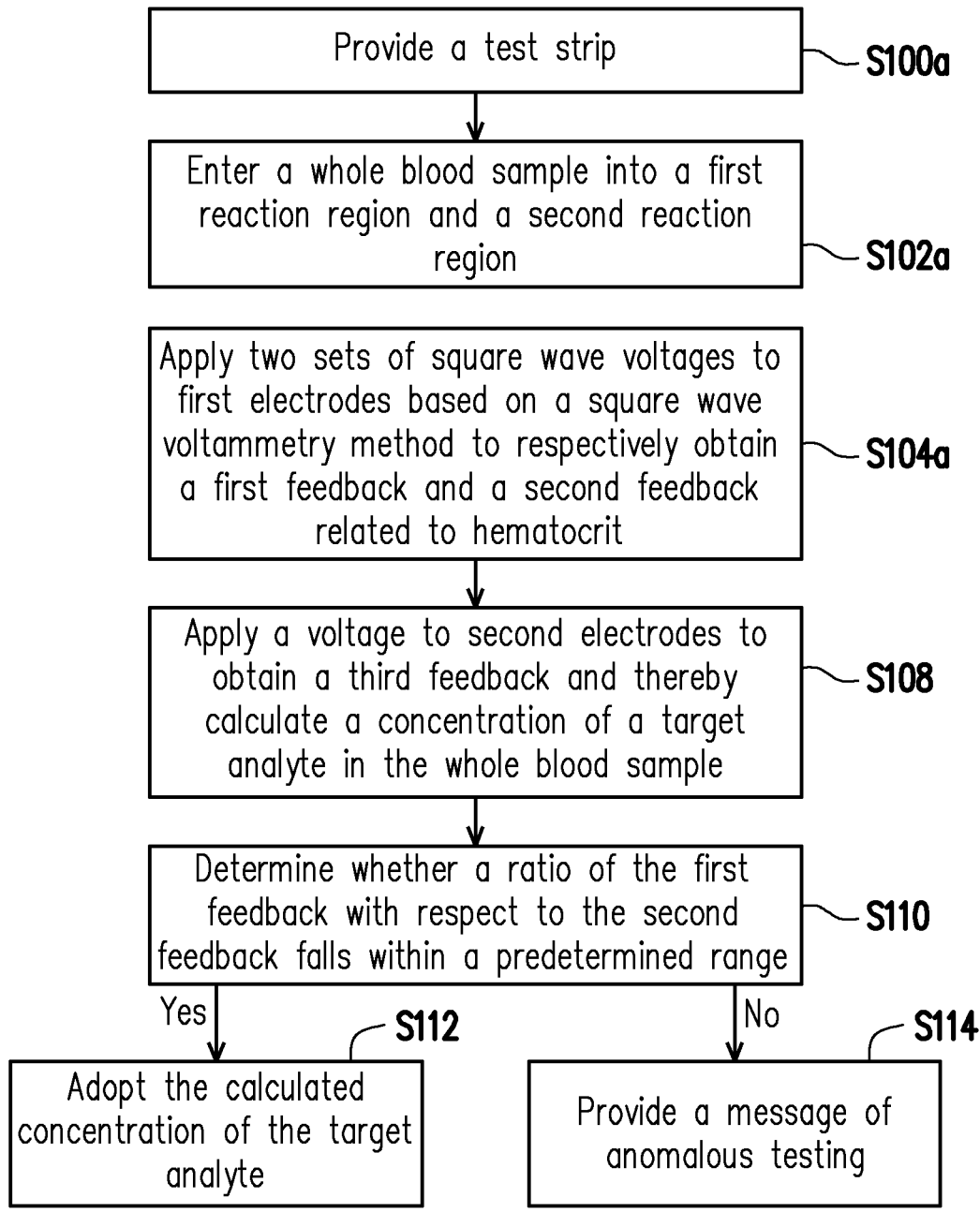
Figure 2:
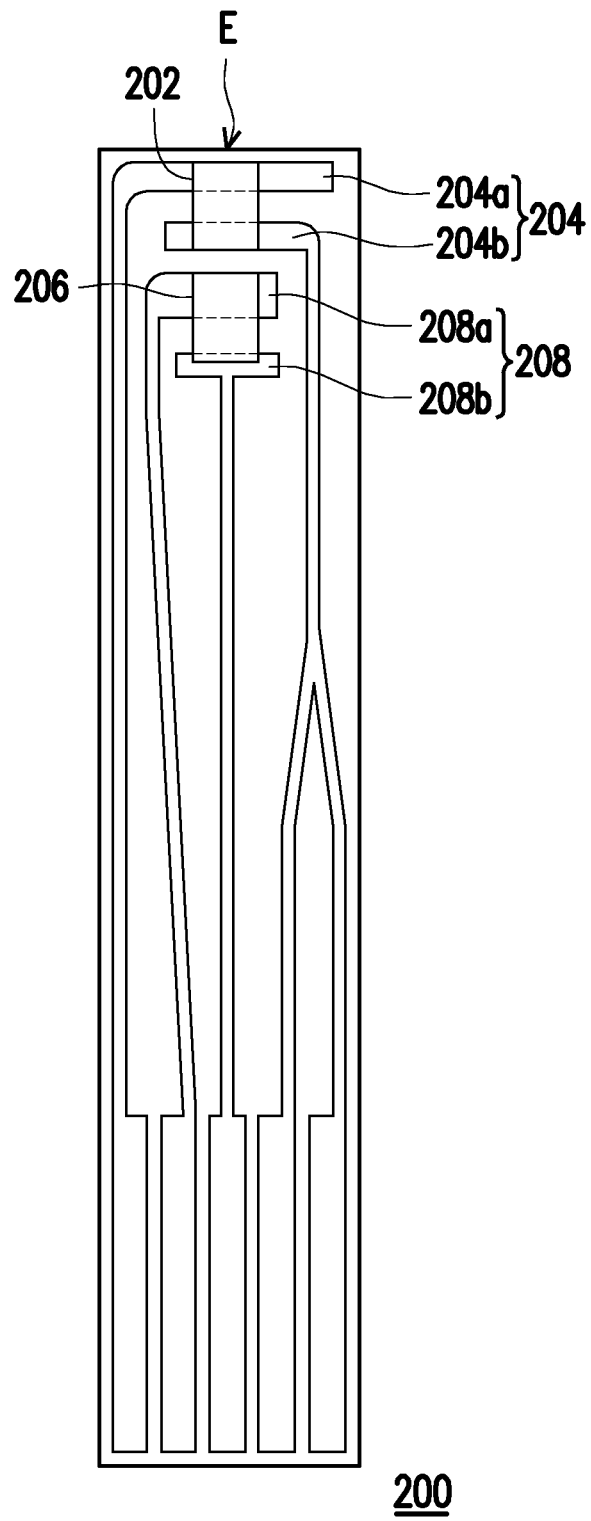
FIG. 2 is a schematic top view illustrating a test strip according to an embodiment of the disclosure.
Figure 3:
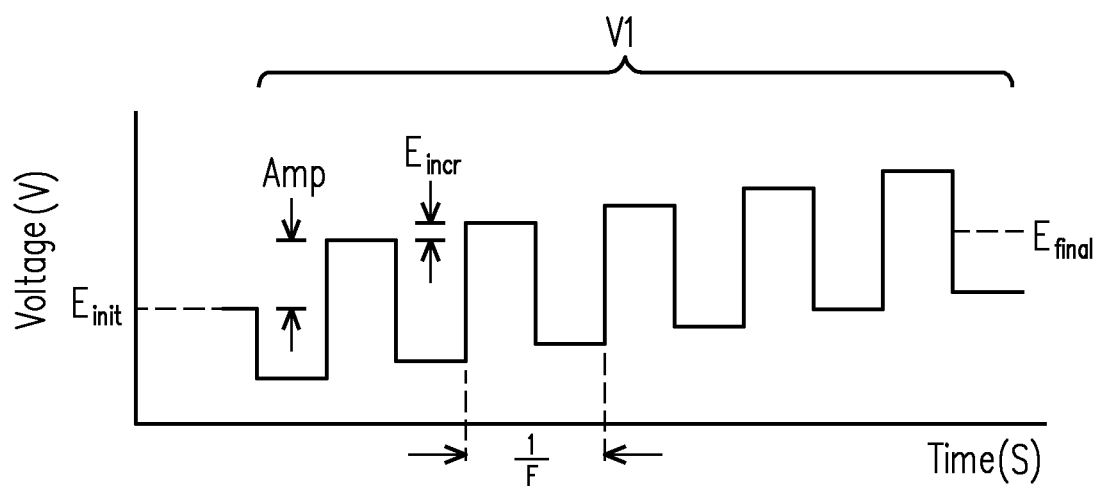
FIG. 3 is a schematic diagram illustrating a voltage of the square wave voltammetry method according to an embodiment of the disclosure changes through time.
Figure 4:
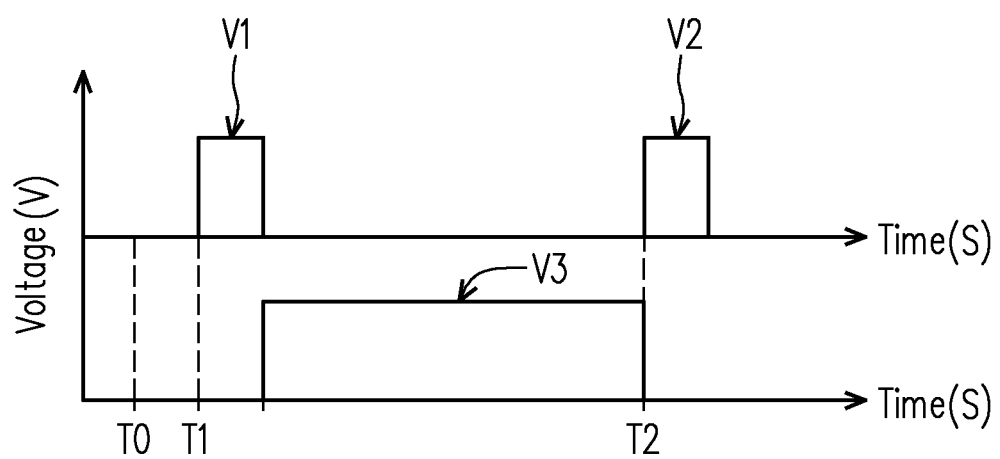
FIG. 4 is a schematic diagram illustrating an order of carrying out a hematocrit measurement and a concentration measurement of a target analyte on a whole blood sample according to the embodiment shown in FIGS. 1A and 1B.

FIGS. 1A and 1B are respectively flowcharts illustrating a method of measuring hematocrit and a method of testing blood according to an embodiment of the disclosure. FIG. 2 is a schematic top view illustrating a test strip according to an embodiment of the disclosure. FIG. 3 is a schematic diagram illustrating a voltage of the square wave voltammetry method according to an embodiment of the disclosure changes through time. FIG. 4 is a schematic diagram illustrating an order of carrying out a hematocrit measurement and a concentration measurement of a target analyte on a whole blood sample according to the embodiment shown in FIGS. 1A and 1B.

Referring to FIGS. 1A and 2, the method of testing hematocrit (Hct) according to an embodiment of the disclosure includes the following steps.

At Step S100, a test strip 200 is provided. The test strip 200 includes a first reaction region 202 and a pair of first electrodes 204 disposed in the first reaction region 202. In some embodiments, the pair of first electrodes 204 includes a first working electrode 204a and a first reference electrode 204b. The first reaction region 202 may be located on the first working electrode 204a and the first reference electrode 204b, and expose a portion of the first working electrode 204a and the first reference electrode 204b. In some embodiments, the testing strip 200 further includes a second reaction region 206 and a pair of second electrodes 208 disposed in the second reaction region 206. The pair of second electrodes 208 may include a second working electrode 208a and a second reference electrode 208b. The second reaction region 206 may be located on the second working electrode 208a and the second reference electrode 208b, and expose a portion of the second working electrode 208a and the second reference electrode 208b.

After a whole blood sample enters the test strip 200 and passes through the first reaction region 202 (or pass through the first reaction region 202 and the second reaction region 206), the first electrodes 204 (or the first electrodes 204 and the second electrodes 208) may receive a voltage, and the whole blood sample may react in the first reaction region 202 (or the first reaction region 202 and the second reaction region 206). In some embodiments, the first reference electrode 204b may be electrically connected with the second reference electrode 208b, or the pair of first electrodes 204 and the pair of second electrodes 208 may share the same reference electrode. In some embodiments, the second reference electrode 208b (or the reference electrode shared with the first reference electrode 204b) may detect an amount of the whole blood sample entering the test strip 200. Accordingly, the voltage may be applied to the first working electrode 204a and the second working electrode 208a for the whole blood sample to react in the first reaction region 202 and the second reaction region 206 after the amount of the whole blood sample is sufficient.

In some embodiments, the first reaction region 202 may be closer to a sample entrance E of the test strip 200 than the second reaction region 206. Besides, the first reaction region 202 and the second reaction region 206 may be disposed in the same channel. However, in other embodiments, the second reaction region 206 may be closer to the sample injection entrance E than the first reaction region 202. Besides, the first reaction region 202 and the second reaction region 206 may also be disposed side-by-side or be disposed on different horizontal levels. Besides, the first reaction region 202 and the second reaction region 206 may be disposed in different channels. People having ordinary skill in the art may adjust relative positions of the first reaction region 202 and the second reaction region 206 based on the design needs. The disclosure does not intend to impose a limitation on this regard.

In some embodiments, a distance between the first working electrode 204a and the first reference electrode 204b ranges from 0.01 mm to 5 mm. For example, the distance between the first working electrode 204a and the first reference electrode 204b may range from 0.01 mm to 1 mm or 0.05 mm to 5 mm. Besides, a ratio of an area of the first working electrode 204a to an area of the first reference electrode 204b may range from 1 to 1.5. For example, the ratio of the area of the first working electrode 204a to the area of the first reference electrode 204b may be in a range from 1 to 1.2. By keeping the distance and the area ratio of the first working electrode 204a and the first reference electrode 204b within these ranges, a stable feedback is able to be obtained when the voltage is applied to the first working electrode 204a.

In some embodiments, a reactive agent may be disposed on the second reaction region 206. The material of the reactive agent may include a reactive enzyme, and may further include an electron mediator. In other embodiments, the reactive reagent may further extend to the first reaction region 202.

At Step 102, the whole blood sample enters the first reaction region 202. The whole blood sample may enter from the sample entrance E of the test strip 200 by means of a capillary force or a microchannel design. Besides, in addition to entering the first reaction region 202, the whole blood sample may further enter the second reaction region 206.

Referring to FIG. 1A and FIGS. 2 to 4, at Step S104, a set of square wave voltages V1 is applied on the pair of first electrodes 204 based on a square wave voltammetry method to obtain a first feedback related to hematocrit. Accordingly, the first working electrode 204a may receive the square wave voltages V1 to induce an electrical reaction of the whole blood sample in the first reaction region 202, so as to obtain a first feedback. The first feedback is a current value. As shown in FIG. 3, the square wave voltages V1 may be positive voltages. An initial voltage $E_{init}$ of the square wave voltages V1 gradually increases through time toward a target voltage $E_{final}$ with an incremental voltage $E_{incr}$. Specifically, the square wave voltages V1 are centered at the initial voltage $E_{init}$, and are applied with a fixed voltage amplitude Amp that swings positively and negatively at a fixed frequency F. Then, the fixed incremental voltage $E_{incr}$ is added, and the square wave voltages V1 then swing with the fixed voltage amplitude by adopting a new voltage value ($E_{init}$+ $E_{incr}$) as the center, until the center of the voltage value reaches the target voltage $E_{final}$.

When the appropriate parameters, such as the amplitude Amp, the frequency F, and the incremental voltage $E_{incr}$, are provided, the first feedback related to hematocrit generated from the whole blood sample is able to be measured stably. In some embodiments, the square wave voltages V1 may be provided with a fixed amplitude Amp, frequency F, and incremental voltage $E_{incr}$. For example, the frequency F may be greater than 100 Hz, such as ranging from 100 Hz to 4000 Hz. The amplitude Amp may be greater than 0.01 V, such as ranging from 0.01 V to 0.4 V. The incremental voltage $E_{incr}$ may range from 0.01 V to 0.4 V, such as ranging from 0.05 V to 0.2 V. In addition, a sweep range of the square wave voltages V1 may range from 0 V to 0.8 V. Furthermore, a duration of voltage application may range from 0.01 seconds to 4 seconds, such as ranging from 0.01 seconds to 2 seconds.

Nevertheless, people having ordinary skills in the art may properly adjust the parameters based on different materials, patterns, locations of the first electrodes 204 and/or other conditions. For example, when the material of the first electrodes 204 includes carbon ink (such as a screen printed carbon electrode, SPCE), the frequency F of the square wave voltage V1 may range from 100 Hz to 500 Hz, and the amplitude Amp may range from 0.01 V to 0.4 V. In addition, the voltage sweep range of the square wave voltage V1 may range from 0 V to 0.5 V, and the duration of application of the square wave voltage V1 may range from 0.01 seconds to 2 seconds. In another example, when the material of the first electrodes 204 includes gold, the frequency F of the square wave voltages V1 may range from 500 Hz to 4000 Hz, and the amplitude Amp may range from 0.1 V to 0.4 V. In addition, the voltage sweep range of the square wave voltage V1 may range from 0 V to 0.5 V, and the duration of application of the square wave voltage V1 may range from 0.01 seconds to 2 seconds.

Referring to FIGS. 3 and 4, a time interval between an initial time T0 when the whole blood sample enters the first reaction region 202 of the test strip 200 and an initial time T1 when the set of square wave voltages V1 is applied to the first electrodes 204 ranges from 0.1 seconds to 200 seconds. In some embodiments, the interval between the initial time T0 and the initial time T1 may also range from 0.1 seconds to 120 seconds, from 0.1 seconds to 60 seconds, from 0.1 seconds to 30 seconds, from 0.1 seconds to 10 seconds, from 0.1 seconds to 5 seconds, from 0.1 seconds to 1 second, from 1 second to 200 seconds, from 3 seconds to 200 seconds, from 5 seconds to 200 seconds, from 10 seconds to 200 seconds, from 20 seconds to 200 seconds, from 50 seconds to 200 seconds, from 1 second to 120 seconds, from 3 seconds to 60 seconds, from 5 seconds to 30 seconds, or from 5 seconds to 10 seconds.

At Step S106, a hematocrit value is calculated based on the first feedback. Experimental findings show that the first feedback (current value) is negatively correlated with the hematocrit value. An equation of the negative correlation may be obtained through statistical computation on the first feedbacks of the whole blood samples with known hematocrit values. The equation may include a polynomial equation or a linear equation. Then, the first feedback of the whole blood sample with an unknown hematocrit value may be substituted into the relational equation to obtain a corresponding hematocrit value.

When the test strip 200 is exposed to the atmosphere, it is likely that a moisture film is formed on the first electrodes 204 (or on the first electrodes 204 and the second electrodes 208). In addition, there may be microbubbles generated between the whole blood sample and the first electrodes 204 (and between the whole blood sample and the second electrodes 208) when the whole blood sample enters the first reaction region 202 of the test strip 200 (or enters the first reaction region 202 and the second reaction region 206). The moisture film and microbubbles may cause errors in the hematocrit measurement. In the embodiment, the moisture film and the microbubbles between the whole blood sample and the first electrodes 204 (and between the whole blood sample and the second electrodes 208) may be destructed by applying the set of square wave voltages V1 to the first electrodes 204 based on the square wave voltammetry method after the whole blood sample stays in the first reaction region 202 for a time interval. Accordingly, the influences of the moisture in the surroundings and the microbubbles on the hematocrit measurement may be avoided. Besides, in the embodiments of the disclosure, when the hematocrit value is measured based on the square wave voltammetry method, the measurement is less susceptible to influences of a concentration of a target analyte (e.g., blood glucose) in the whole blood sample. Therefore, the method according to one or some embodiments of the disclosure is able to reduce errors in a hematocrit measurement caused by moisture, microbubbles, and concentration of target analyte in the whole blood sample.

Referring to FIG. 1B and FIGS. 2 to 4, the method of testing blood according to an embodiment of the disclosure includes the following steps. The method of testing blood according to the embodiment includes part of the method of measuring hematocrit shown in FIG. 1A. Thus, like or similar parts will not be repeated in the following. Moreover, similar steps are marked with similar reference symbols.

At Step S100a, the test strip 200 is provided. As shown in FIG. 2, the test strip 200 includes the first reaction region 202, the pair of first electrodes 204 disposed in the first reaction region 202, the second reaction region 206, and the pair of second electrodes 208 disposed in the second reaction region 206.

At Step 102a, the whole blood sample enters the first reaction region 202 and the second reaction region 206. Then, at Step S104a, the set of square wave voltages V1 and a set of square wave voltages V2 are applied to the first electrodes 204 based on the square wave voltammetry method to obtain the first feedback and a second feedback related to hematocrit. Specifically, the first working electrode 204a may respectively receive the square wave voltages V1 and the square wave voltages V2 to induce an electrical reaction of the whole blood sample in the first reaction region 202, so as to obtain the first feedback and the second feedback related to hematocrit. In addition, the square wave voltages V2 are similar to the square wave voltages V1, except for a difference regarding the timings at which the square wave voltages V1 and the square wave voltages V2 are applied. The initial time T1 when the square wave voltages V1 are applied is earlier than an initial time T2 when the square wave voltages V2 are applied. In some embodiments, an interval between the initial time T1 of the square wave voltages V1 and the initial time T2 of the square wave voltages V2 may range from 0.1 seconds to 200 seconds. In some other embodiments, an interval between the initial time T1 of the square wave voltages V1 and the initial time T2 of the square wave voltages V2 may range from 0.1 seconds to 3 seconds.

At Step S108, a voltage V3 is applied to the second electrodes 208 to obtain a third feedback and thereby calculate a concentration of a target analyte in the whole blood sample. In some embodiments, the voltage V3 may be applied to the second electrodes 208 after or before the square wave voltages V1 are applied. In some other embodiments, the voltage V3 may be applied to the second electrodes 208 immediately or a while after the square wave voltages V1 are applied. In another embodiment, the voltage V3 may be applied to the second electrodes 208 after the square wave voltages V2 are applied. The voltage V3 may be applied independently at an arbitrary point of time. The disclosure does not intend to impose a limitation on this regard. The voltage V3 may be applied to the second electrodes based on a amperometry method, a coulometry method, a potentiometry method, a voltammetry method, an impedance method, or a combination thereof. The disclosure does not intend to impose a limitation on this regard. In some embodiments, the target analyte includes blood glucose, glycated hemoglobin (HbAlc), blood lactic acid, cholesterol, uric acid, triglyceride, coagulation factor, or anticoagulant.

Calculating the concentration of the target analyte in the whole blood sample based on the third feedback includes calculating the hematocrit value in the whole blood sample based on at least one of the first feedback and the second feedback (e.g., Step S106 of FIG. 1A). In some embodiments, the hematocrit value of the whole blood sample may be calculated based on the first feedback, the second feedback, or an average of the first feedback and the second feedback. Then, the concentration of the target analyte is calculated based on the hematocrit value obtained through calculation and the third feedback. By testing whole blood samples with different hematocrit values, different linear equations between the concentration of the target analyte and the third feedback may be obtained. Relations between slopes and constant terms of the linear equations may be calibrated by the hematocrit value obtained through calculation, so as to derive a general equation of the concentration of the target analyte and the third feedback. Accordingly, by substituting the third feedback into the general equation, the concentration of the target analyte can be obtained.

Then, at Step S110, whether a ratio of the first feedback with respect to the second feedback falls within a predetermined range is determined. In some embodiments, the predetermined range may range from 0.85 to 1.18. If the ratio of the first feedback with respect to the second feedback falls within the predetermined range, the calculated concentration of the target analyte is adopted at Step S112. Alternatively, if the ratio of the first feedback with respect to the second feedback is less or greater than the predetermined range, Step S114 is performed to provide a message of anomalous testing. In other words, the calculated concentration of the target analyte is adopted when the ratio of the first feedback with respect to the second feedback falls within the predetermined range, and is not adopted if the ratio of the first feedback with respect to the second feedback does not fall within the predetermined range. Accordingly, an influence of external factors on calculating the concentration of the target analyte may be eliminated, so as to avoid a misjudgment. In general, the external factors may include temperature/humidity variations in the surroundings or defects in the test strip 200.

Based on the above, in the method of measuring hematocrit according to the embodiment, the square wave voltages V1 are applied to the first electrodes 204 by adopting the square wave voltammetry method after the whole blood sample stays in the first reaction region 202 for a time interval. Accordingly, the moisture film and the microbubbles between the whole blood sample and the first electrode 204 (and between the whole blood sample and the second electrode 208) may be destructed. As a result, the influences of the moisture in the surroundings and the microbubbles on the hematocrit measurement are reduced. In addition, the square wave voltammetry method applied for measuring hematocrit is less susceptible to influences of the concentration of the target analyte. Therefore, the hematocrit value obtained is more accurate. Besides, in the method of testing blood according to the embodiment, the concentration of the target analyte in the whole blood sample is calculated from the obtained hematocrit value and the third feedback obtained by applying the voltage V3 to the second electrodes 208. Moreover, whether the concentration of the target analyte calculated based on the third feedback is adopted is determined based on whether the ratio of the first feedback with respect to the second feedback falls within the predetermined range, so as to reduce the influence of external factors on the calculation of the concentration of the target analyte.

Figure 5A:
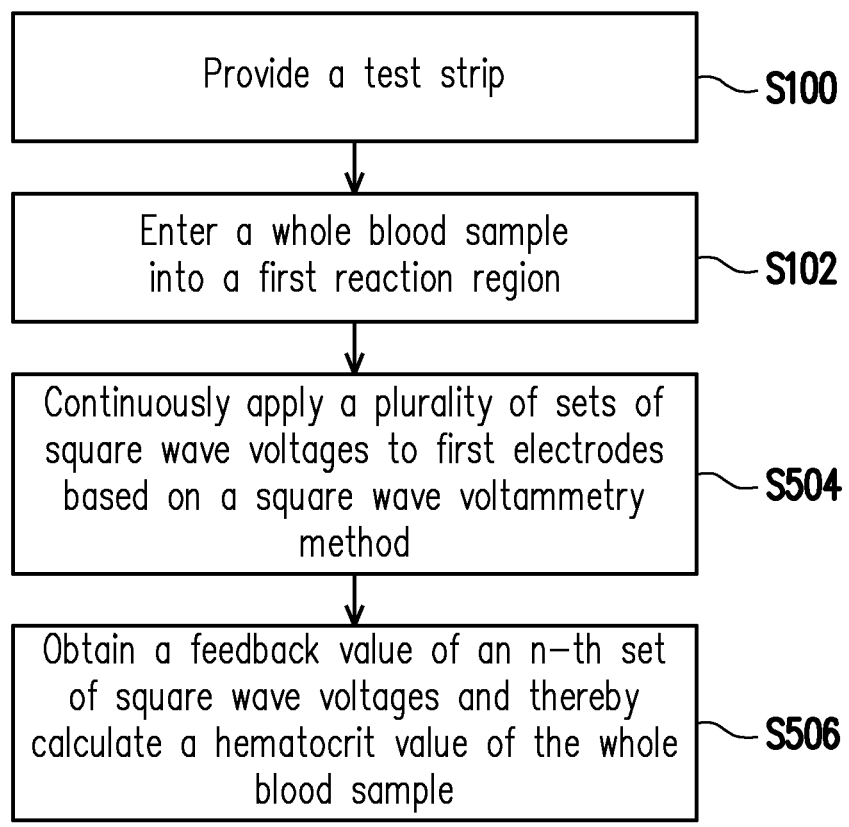
FIGS. 5A and 5B are respectively flowcharts illustrating a method of measuring hematocrit and a method of testing blood according to another embodiment of the disclosure.
Figure 5B:
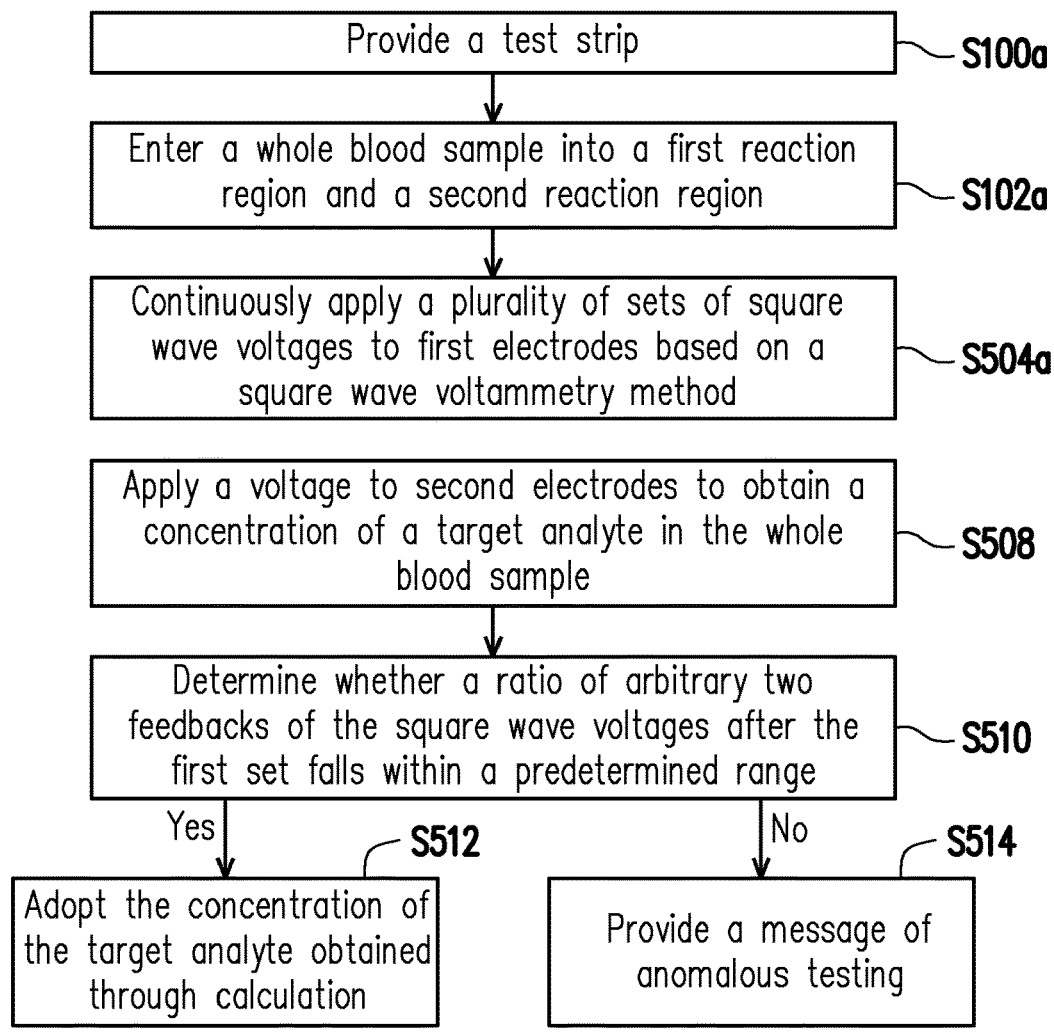
Figure 6:
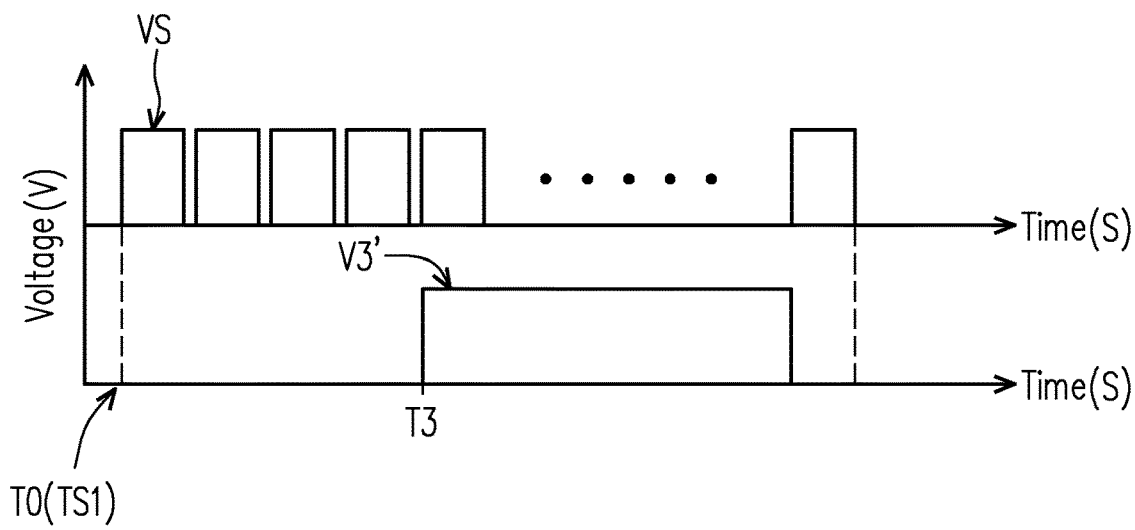
FIG. 6 is a schematic diagram illustrating an order of carrying out a hematocrit measurement and a concentration measurement of a target analyte on a whole blood sample according to the embodiment shown in FIGS. 5A and 5B.

FIGS. 5A and 5B are respectively flowcharts illustrating a method of measuring hematocrit and a method of testing blood according to another embodiment of the disclosure. FIG. 6 is a schematic diagram illustrating an order of carrying out a hematocrit measurement and a concentration measurement of a target analyte on a whole blood sample according to the embodiment shown in FIGS. 5A and 5B.

Referring to FIGS. 5A and 6, the method of measuring hematocrit according to another embodiment of the disclosure is similar to the method of measuring hematocrit shown in FIG. 1A. Therefore, the following steps only focus on the difference, while like or similar parts will not be repeated in the following.

Referring to FIGS. 2, 5A, and 6, after Step S100 and Step S102, Step S504 is carried out to continuously apply a plurality of sets of square wave voltages VS (e.g., a plurality of square wave voltages shown in FIG. 6) to the first electrodes 204 based on the square wave voltammetry method. An interval between two adjacent sets of square wave voltages VS ranges from 0.1 seconds to 4 seconds. Each set of square wave voltages VS may be equivalent to the square wave voltages V1 shown in FIG. 3. The difference between the sets of square wave voltages VS only lies in the timing at which the respective sets of square wave voltages VS are applied. Accordingly, the first working electrode 204a may receive the continuous sets of square wave voltages VS to induce electrical reactions of the whole blood sample in the first reaction region 202, so as to obtain a plurality of feedbacks related to hematocrit.

In some embodiments, the initial time T0 when the whole blood sample enters the first reaction region 202 (or enters the first reaction region 202 and the second reaction region 206) is equivalent to an initial time TS1 when the first set of square wave voltages VS is applied to the first electrodes 204. For example, the initial time T0 is a time at which the amount of the whole blood sample in the first reaction region 202 (or in the first reaction region 202 and the second reaction region 206) reaches a threshold. People having ordinary skill in the art may adjust the threshold based on testing requirements. The disclosure does not intend to impose a limitation on this regard. In other words, in the above embodiment, when the whole blood sample enters the first reaction region 202 (or the first reaction region 202 and the second reaction region 206), the first set of square wave voltages VS is immediately applied to the first electrodes 204. Nevertheless, in other embodiments, the first set of square wave voltages VS may be applied to the first electrodes 204 after the whole blood sample fills up the first reaction region 202 (or enters the first reaction region 202 and the second reaction region 206). To put it differently, the initial time TS1 may follow the initial time T0. People having ordinary skill in the art may adjust the order between the initial time TS1 and the initial time T0 based on testing requirements. The disclosure does not intend to impose a limitation on this regard.

At Step S506, a feedback of an n-th set of square wave voltages VS is obtained, so as to calculate the hematocrit value of the whole blood sample. Here, n is a positive integer greater than 1. In some embodiments, obtaining the feedback of the n-th set of square wave voltages VS includes obtaining a feedback of an arbitrary set of square wave voltages VS after the first set or obtaining an average feedback of a plurality of sets of square wave voltages VS after the first set. The reason of obtaining the feedback of the square wave voltages VS after the first set is that the feedback of the first set of square wave voltages VS are more susceptible to influences of external factors. In other words, the feedback of the square wave voltages VS after the first set may become stabilized, and a more accurate hematocrit value may be obtained accordingly. In some embodiments, n is a positive integer greater than or equal to 3. People having ordinary skill in the art may calculate the hematocrit value by choosing the feedback of an arbitrary set of square wave voltages VS after the first set or the average feedback of a plurality of sets after the first set. The disclosure does not intend to impose a limitation on this regard. Besides, a method of calculating the hematocrit value based on the feedback of the n-th set of square wave voltages VS may be referred to the descriptions of Step S106 in FIG. 1A.

Similar to the method of measuring hematocrit shown in FIG. 1A, the method of measuring hematocrit according to the present embodiment also destructs the moisture film and microbubbles between the whole blood sample and the first electrodes 204 (and between the whole blood sample and the second electrodes 208) by applying the square wave voltages VS for multiple times. Accordingly, the influences of the moisture in the surroundings and microbubbles on the hematocrit measurement may be reduced.

Referring to FIGS. 5B and 6, the method of testing blood according to the embodiment is similar to the method of blood testing shown in FIG. 1B and includes the method of measuring hematocrit shown in FIG. 5A. To keep the descriptions concise, like or similar parts will not be repeated in the following.

After Step S100a and Step S102a, Step S504a is carried out to continuously apply the sets of square wave voltages VS to the first electrodes 204 based on the square wave voltammetry method. An interval between two adjacent sets of square wave voltages VS ranges from 0.1 seconds to 4 seconds. Each set of square wave voltages VS may be equivalent to the square wave voltages V1 shown in FIG. 3. The difference between the sets of square wave voltages VS only lies in the timing at which the respective sets of square wave voltages VS are applied. Accordingly, the first working electrode 204a may receive the continuous sets of square wave voltages VS to induce electrical reactions of the whole blood sample in the first reaction region 202, so as to obtain a plurality of feedbacks related to hematocrit.

At Step S508, a voltage V3' is applied to the second electrodes 208 to calculate the concentration of the target analyte in the whole blood sample. In some embodiments, the initial time TS1 of the first set of square wave voltages VS may precede an initial time T3 of the voltage V3'. The initial time TS1 of the first set of square wave voltages VS may be equivalent to the initial time T0 when the whole blood sample enters the first reaction region 202, or follow the initial time T0. Besides, the initial time T3 of the voltage V3' may follow the n-th set of square wave voltages VS. Here, n is a positive integer greater than 1. In some embodiments, n is a positive integer greater than or equal to 3. In other embodiments, the initial time TS1 of the first set of square wave voltages VS may follow the initial time T3 of the voltage V3' or be equivalent to the initial time T3 of the voltage V3'. It should be noted that the disclosure does not intend to impose a limitation on this regard.

At Step S508, calculating the concentration of the target analyte in the whole blood sample may include calculating the hematocrit value in the whole blood sample based on the feedback of an arbitrary set of square wave voltages VS after the first set or the average feedback of a plurality of sets of square wave voltages VS after the first set. Then, a general equation of the concentration of the target analyte and the voltage V3' is obtained in a way similar to Step S108 shown in FIG. 1B. Accordingly, by substituting the feedback of the voltage V3' into the general equation, the concentration of the target analyte can be obtained.

Then, at Step S510, whether a ratio of arbitrary two feedbacks of the square wave voltages after the first set falls within a predetermined range is determined. In some embodiments, the predetermined range may range from 0.85 to 1.18.

If the ratio of the arbitrary two feedbacks of the square wave voltages after the first set falls within the predetermined range, the calculated concentration of the target analyte is adopted at Step S512. Alternatively, if the ratio of the arbitrary two feedbacks of the square wave voltages after the first set is not within the predetermined range but less or greater than the predetermined range, Step S514 is performed to provide a message indicating anomalous testing.

Similar to the method of testing blood shown in FIG. 1B, the method of testing blood according to the embodiment may also eliminate the influences of external factors on calculating the concentration of the target analyte by carrying out Step S510, Step S512, and Step S514.

In the following, the effect of one or some embodiments of the disclosure are described with reference to experimental examples and comparative examples.

Experimental Example 1

Step S100, Step S102, and Step S104 shown in FIG. 1A were respectively performed on whole blood samples having different hematocrit values and different blood glucose contents. Referring to FIGS. 2 to 4, the initial voltage $E_{init}$ of the square wave voltages V1 of Experimental Example 1 was set at 0 V, the fixed voltage amplitude Amp was set at 0.01 V, the incremental voltage $E_{incr}$ was set at 0.01 V, and the frequency F was set at 300 Hz. In addition, the interval between the initial time T0 when the whole blood samples entered the first reaction region 202 of the test strip 200 and the initial time T1 when the set of square wave voltages V1 was applied to the first electrodes 204 was set at 0.5 seconds.

Comparative Example 1

In Comparative Example 1, feedbacks were obtained by applying voltages to the whole blood samples having different hematocrit values and different blood glucose contents based on a differential pulse voltammetry method. An initial voltage of the differential pulse voltammetry method was set at 0 V, a fixed voltage amplitude was set at 0.05 V, an incremental voltage was set at 0.045 V, and a time interval was set at 0.02 seconds. In addition, an interval between the initial time when the whole blood samples entered the first reaction region 202 of the test strip 200 and the initial time when the voltage was applied to the first electrodes 204 based on the differential pulse voltammetry method was set at 0.5 seconds.

Comparison Between Experimental Example 1 and Comparative Example 1

Table 1 sorts the results of Experimental Example 1, whereas Table 2 sorts the results of Comparative Example 1.

TABLE 1

| | Hematocrit (%) | Blood glucose contents (mg/dL) | Current feedback (A) |
|---|---|---|---|
| Whole Blood Sample 1 | 0 | 44 | 1.21E−05 |
| Whole Blood Sample 2 | 0 | 81 | 1.16E−05 |
| Whole Blood Sample 3 | 0 | 216 | 1.26E−05 |
| Whole Blood Sample 4 | 0 | 325 | 1.23E−05 |
| Whole Blood Sample 5 | 0 | 507 | 1.22E−05 |
| Whole Blood Sample 6 | 20 | 44 | 1.19E−05 |
| Whole Blood Sample 7 | 20 | 81 | 1.13E−05 |
| Whole Blood Sample 8 | 20 | 216 | 1.19E−05 |
| Whole Blood Sample 9 | 20 | 325 | 1.20E−05 |
| Whole Blood Sample 10 | 20 | 507 | 1.19E−05 |
| Whole Blood Sample 11 | 42 | 44 | 1.10E−05 |
| Whole Blood Sample 12 | 42 | 81 | 1.06E−05 |
| Whole Blood Sample 13 | 42 | 216 | 1.12E−05 |
| Whole Blood Sample 14 | 42 | 325 | 1.11E−05 |
| Whole Blood Sample 15 | 42 | 507 | 1.12E−05 |
| Whole Blood Sample 16 | 55 | 44 | 1.06E−05 |
| Whole Blood Sample 17 | 55 | 81 | 1.05E−05 |
| Whole Blood Sample 18 | 55 | 216 | 1.07E−05 |
| Whole Blood Sample 19 | 55 | 325 | 1.03E−05 |
| Whole Blood Sample 20 | 55 | 507 | 1.07E−05 |
| Whole Blood Sample 21 | 70 | 44 | 9.96E−06 |
| Whole Blood Sample 22 | 70 | 81 | 9.37E−06 |
| Whole Blood Sample 23 | 70 | 216 | 1.02E−05 |
| Whole Blood Sample 24 | 70 | 325 | 1.05E−05 |
| Whole Blood Sample 25 | 70 | 507 | 1.05E−05 |

TABLE 2

| | Hematocrit (%) | Blood glucose contents (mg/dL) | Current feedback (A) |
|---|---|---|---|
| Whole Blood Sample 26 | 0 | 79 | 4.43E−06 |
| Whole Blood Sample 27 | 0 | 197 | 9.95E−06 |
| Whole Blood Sample 28 | 0 | 383 | 1.56E−05 |
| Whole Blood Sample 29 | 20 | 79 | 3.62E−06 |
| Whole Blood Sample 30 | 20 | 197 | 7.55E−06 |
| Whole Blood Sample 31 | 20 | 383 | 1.45E−05 |
| Whole Blood Sample 32 | 43 | 79 | 3.11E−06 |
| Whole Blood Sample 33 | 43 | 197 | 7.02E−06 |
| Whole Blood Sample 34 | 43 | 383 | 1.14E−05 |
| Whole Blood Sample 35 | 70 | 79 | 2.80E−06 |
| Whole Blood Sample 36 | 70 | 197 | 4.26E−06 |
| Whole Blood Sample 37 | 70 | 383 | 8.00E−06 |

According to Table 1 and Table 2, in Comparative Example 1 using the differential pulse voltammetry method, the current feedbacks obtained from the samples with the same blood glucose concentration are able to differentiate the difference in hematocrit among the samples. However, in samples with the same hematocrit value but different blood glucose contents, the current feedbacks obtained based on the differential pulse voltammetry method are significantly positively correlated with the blood glucose contents in the samples, while the positive correlative relationship between the current feedbacks and the blood glucose contents is less significant in Experimental Example 1 using the square wave voltammetry method. Accordingly, compared with the differential pulse method, the square wave voltammetry method is less sensitive to the blood glucose content in the whole blood sample. Therefore, when measuring hematocrit in the sample, the square wave voltammetry method is less susceptible to the interference of the current variation caused by blood glucose concentration. Therefore, the hematocrit value of the whole blood sample is able to be measured more accurately.

Experimental Example 2

Step S100, Step S102, and Step S104 shown in FIG. 1A were respectively performed on whole blood samples A to E having known but different hematocrit values. The known hematocrit value of the whole blood sample A was 20%, the known hematocrit value of the whole blood sample B was 31%, the known hematocrit value of the whole blood sample C was 40%, the known hematocrit value of the whole blood sample D was 51%, and the known hematocrit value of the whole blood sample E was 60%. Referring to FIGS. 2 and 4, the initial voltage $E_{init}$ of the square wave voltages V1 of Experimental Example 2 was set at 0.15 V, the fixed voltage amplitude Amp was set at 0.17 V, the incremental voltage $E_{incr}$ was set at 0.04 V, and the frequency F was set at 750 Hz. In addition, the interval between the initial time T0 when the whole blood samples entered the first reaction region 202 of the test strip 200 and the initial time T1 when the set of square wave voltages V1 was applied to the first electrodes 204 was set at 5 seconds.

Comparative Example 2

Comparative Example 2 is similar to Experimental Example 2, and the two examples only differ in that the initial time T0 was equivalent to the initial time T1 in the comparative example. In other words, there was no time interval between the initial time T0 and the initial time T1. Hence, the square wave voltages V1 were immediately applied to the first electrodes 204 when the whole blood sample entered the first reaction region 202 of the test strip 200.

Comparison Between Experimental Example 2 and Comparative Example 2

Table 3 sorts the results of Experimental Example 2 and Comparative Example 2.

TABLE 3

| Feedback of square wave voltage V1 | <Experiment 2> | Comparative Example 2 |
|---|---|---|
| Feedback of whole blood sample A (Hematocrit = 20%) | 2546 | 1558 |
| Feedback of whole blood sample B (Hematocrit = 31%) | 2387 | 1603 |
| Feedback of whole blood sample C (Hematocrit = 40%) | 2310 | 1538 |
| Feedback of whole blood sample D (Hematocrit = 51%) | 2197 | 1658 |
| Feedback of whole blood sample E (Hematocrit = 60%) | 2099 | 1623 |

In general, the feedbacks of the square wave voltages and the hematocrit values of the whole blood samples are negatively correlated. According to Table 3, the results of Experimental Example 2 meet the negatively correlated relationship. Comparatively, the negatively correlated relationship is not available based on the results of Comparative Example 2. Accordingly, applying the set of square wave voltages V1 to the first electrodes 204 based on the square wave voltammetry method after the whole blood sample stays in the first reaction region 202 for a time interval is able to facilitate the accuracy of the hematocrit measurement and/or the accuracy of blood testing.

Experimental Example 3

In Experimental Example 3, Step S100, Step S102, and Step S104 shown in FIG. 5A were respectively performed in environments with different humidity levels. In Experimental Example 3, the sets of square wave voltages VS were continuously applied to the first electrodes based on the square wave voltammetry method, and the interval between two adjacent sets of square wave voltages VS was set at one second. Thereafter, the hematocrit values of whole blood samples were calculated based on the feedback of the third set of square wave voltages VS. Before the above-mentioned steps are performed, an apparatus configured to apply the voltages on the first electrodes 204 of the test strip 200 was placed in environments with relative humidities respectively at 31%, 60%, and 90% and was hold for 30 minutes. Then, Steps S100, Step 102, and Step S504 were respectively performed on whole blood samples having different hematocrit values (20%, 31%, 40%, 50%, and 59%, respectively). At Step S504, the initial voltage $E_{init}$ of the square wave voltages VS was set at 0.1 V, and the target voltage $E_{final}$ was set at 0.4 V.

Figure 7:
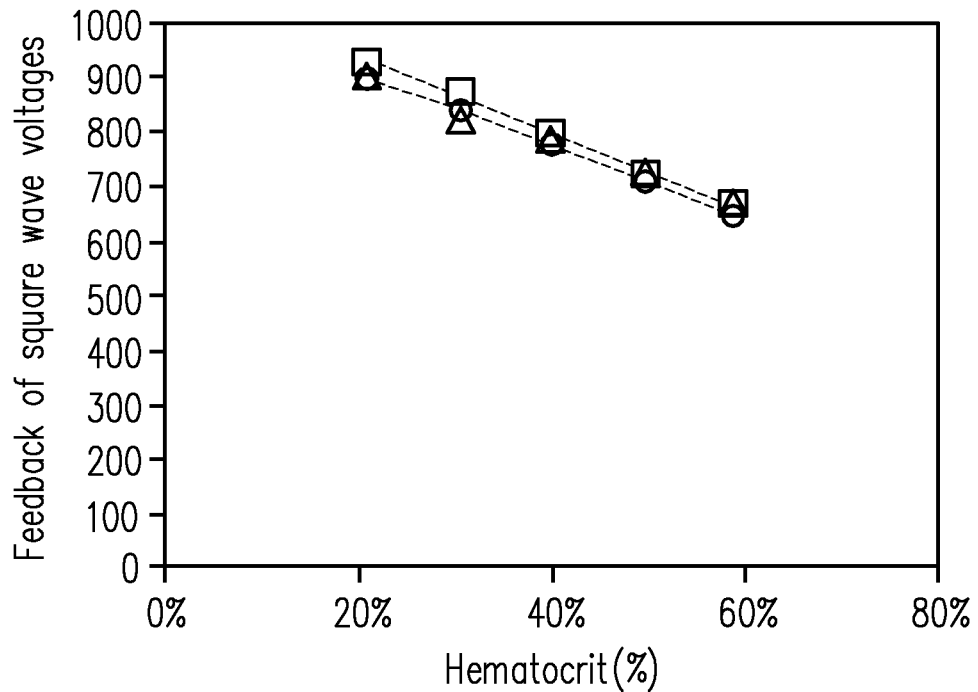
FIG. 7 is a diagram illustrating feedbacks of square wave voltages and hematocrit values under different humidity levels according to an experimental example of the disclosure.

FIG. 7 is a diagram illustrating feedbacks of square wave voltages and hematocrit values under different humidity levels according to Experimental Example 3 of the disclosure.

The vertical axis of FIG. 7 represents the feedbacks of the square wave voltages VS, and the horizontal axis represents the hematocrit value. In addition, square data points represent the third feedbacks of the square wave voltages VS at the relative humidity of 60%, round data points represent the third feedbacks of the square wave voltages VS at the relative humidity of 31%, and triangular data points represent the third feedbacks of the square wave voltages VS at the relative humidity of 90%.

Comparative Example 3

Comparative Example 3 was similar to Experimental Example 3, except that the feedbacks of the first set of square wave voltages VS were adopted to calculate the hematocrit values of whole blood samples.

Figure 8:
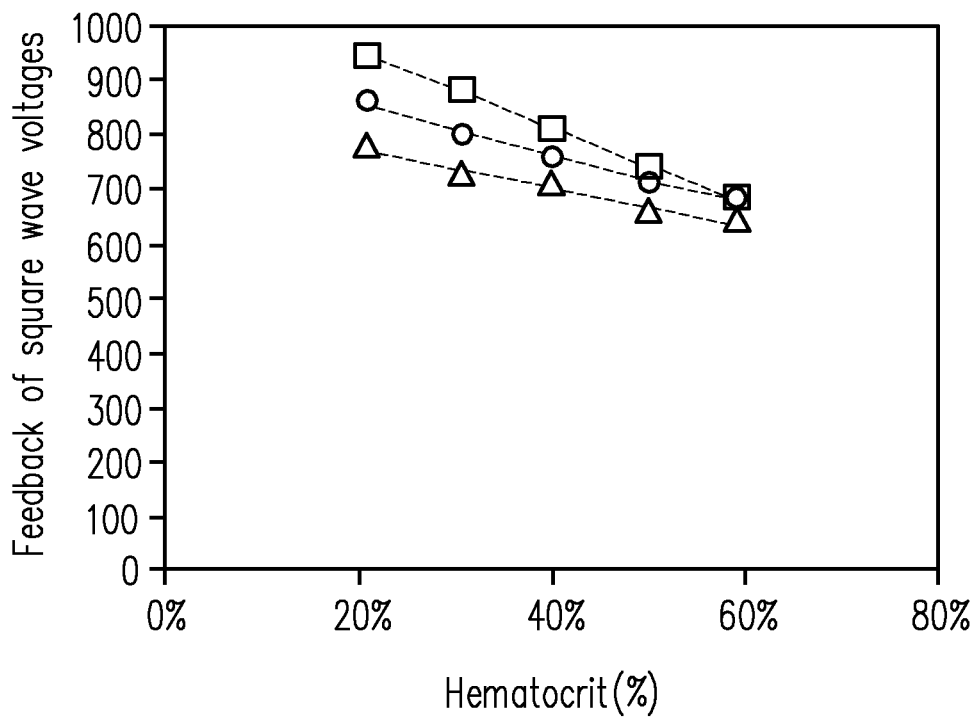
FIG. 8 is a diagram illustrating feedbacks of square wave voltages and hematocrit values under different humidity levels according to a comparative example.

FIG. 8 is a diagram illustrating feedbacks of square wave voltages and hematocrit values under different humidity levels according to Comparative Example 3.

The vertical axis of FIG. 8 represents the feedbacks of the square wave voltages VS, and the horizontal axis represents the hematocrit value. In addition, square data points represent the first feedbacks of the square wave voltages VS at the relative humidity of 90%, round data points represent the first feedbacks of the square wave voltages VS at the relative humidity of 60%, and triangular data points represent the first feedbacks of the square wave voltages VS at the relative humidity of 31%.

Comparison Between Experimental Example 3 and Comparative Example 3

Table 4 sorts the data of Experimental Example 3 shown in FIG. 7, whereas Table 5 shorts the results of Comparative Example 3 shown in FIG. 8.

TABLE 4

| Hematocrit | Feedback corresponding to relative humidity at 31% | Coefficient of variation corresponding to relative humidity at 31% | Feedback corresponding to relative humidity at 60% | Coefficient of variation corresponding to relative humidity at 60% | Feedback corresponding to relative humidity at 90% | Coefficient of variation corresponding to relative humidity at 90% |
|---|---|---|---|---|---|---|
| 21% | 893.9 | 2.2% | 923.4 | 3.3% | 894.0 | 2.2% |
| 31% | 836.6 | 2.7% | 872.1 | 2.5% | 812.9 | 3.1% |
| 40% | 781.8 | 2.0% | 797.3 | 1.7% | 780.0 | 2.7% |

TABLE 4-continued

| Hematocrit | Feedback corresponding to relative humidity at 31% | Coefficient of variation corresponding to relative humidity at 31% | Feedback corresponding to relative humidity at 60% | Coefficient of variation corresponding to relative humidity at 60% | Feedback corresponding to relative humidity at 90% | Coefficient of variation corresponding to relative humidity at 90% |
|---|---|---|---|---|---|---|
| 50% | 693.6 | 1.4% | 719.8 | 1.6% | 722.8 | 1.2% |
| 59% | 646.6 | 2.3% | 663.4 | 2.1% | 662.3 | 2.9% |

TABLE 5

| Hematocrit | Feedback corresponding to relative humidity at 31% | Coefficient of variation corresponding to relative humidity at 31% | Feedback corresponding to relative humidity at 60% | Coefficient of variation corresponding to relative humidity at 60% | Feedback corresponding to relative humidity at 90% | Coefficient of variation corresponding to relative humidity at 90% |
|---|---|---|---|---|---|---|
| 21% | 773.6 | 1.8% | 861.9 | 2.0% | 947.4 | 1.4% |
| 31% | 712.6 | 2.7% | 798.4 | 1.1% | 879.4 | 2.4% |
| 40% | 695.3 | 2.6% | 749.4 | 2.0% | 805.6 | 2.6% |
| 50% | 643.9 | 2.0% | 707.1 | 5.1% | 731.9 | 2.0% |
| 59% | 628.3 | 1.9% | 670.9 | 1.3% | 670.1 | 2.0% |

According to Table 4 and Table 5, the feedbacks of Experimental Example 3 and Comparative Example 3 substantially show a negative correlative relationship between the feedbacks and the hematocrit values in the whole blood samples. When the hematocrit values were the same, the feedbacks at different relative humidities in Experimental 3 were consistent. Taking the samples with the hematocrit value of 21% as an example, the greatest difference among the feedbacks at the relative humidities of 31%, 60%, and 90% in Experimental Example 3 was only 29.5. Comparatively, when the hematocrit values were the same, Comparative Example 3 shows a greater variance among the feedbacks at different relative humidities. Taking the samples with the hematocrit value of 21% as an example, the greatest difference among the feedbacks at the relative humidities of 31%, 60%, and 90% in Comparative Example 3 was 173.8. Hence, based on Experimental Example 3 and Comparative Example 3, by applying voltages to test the whole blood sample based on the square wave voltammetry method and calculating the hematocrit value based on the feedback after the first set according to the embodiments of the disclosure, the influence of the moisture in the surroundings on the test results can be reduced.

In view of the foregoing, in the method of measuring hematocrit according to the embodiments of the disclosure, the square wave voltages are applied to the first electrodes of the test strip based on the square wave voltammetry method after the whole blood sample stays in the first reaction region for a time interval, or a plurality of sets of square wave voltages is continuously applied to the first electrodes based on the square wave voltammetry method. Accordingly, the moisture film and the microbubbles between the whole blood sample and the electrodes are able to be effectively destructed. As a result, the influence of the moisture in the surroundings and the microbubbles on the hematocrit measurement is able to be reduced, and the hematocrit value obtained through measurement is more accurate. Besides, in the embodiments of the disclosure, when the hematocrit value is measured based on the square wave voltammetry method, the measurement is less susceptible to the influences of the concentration of the target analyte.

In the method of testing blood according to the embodiments of the disclosure, the concentration of the target analyte in the whole blood sample is calculated based on the hematocrit value obtained through measurement and another feedback obtained by applying a voltage to the second electrodes. In some embodiments, whether the concentration of the target analyte calculated based on the feedback is adopted is determined by whether the ratio of the feedbacks of two sets of square wave voltages fall within a specific range. In one or some embodiments where a plurality of sets of square wave voltages is continuously applied, whether the concentration of the target analyte calculated based on the feedbacks is adopted is determined by whether the ratio of arbitrary two feedbacks of the square wave voltages after the first set fall within a specific range. Accordingly, the method of testing blood according to the embodiments of the disclosure is able to eliminate the influence of external factors on calculating the concentration of the target analyte.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method of measuring hematocrit, comprising:
providing a test strip comprising a reaction region and a pair of electrodes disposed in the reaction region;
entering a whole blood sample into the reaction region;
intermittently applying a plurality of sets of square wave voltages to the pair of electrodes based on a square wave voltammetry method to obtain a plurality of feedbacks related to hematocrit, wherein an interval between two adjacent sets of square wave voltages ranges from 0.1 seconds to 4 seconds, each set of square wave voltages comprises multiple constant square wave voltages, and there is an interval between two adjacent sets of square wave voltages;

obtaining a feedback of an n-th set of square wave voltages to calculate a hematocrit value of the whole blood sample, wherein n is a positive integer greater than 1.

2. The method of measuring hematocrit as claimed in claim 1, wherein the step of calculating the hematocrit value comprises:

obtaining a general equation of feedback value with respect to hematocrit value by using standard whole blood samples with known hematocrit values; and substituting the feedback of the n-th set of square wave voltages of the whole blood sample for the feedback value to obtain the corresponding hematocrit value.

3. The method of measuring hematocrit as claimed in claim 1, wherein the pair of electrodes comprise a working electrode and a reference electrode, a distance between the working electrode and the reference electrode ranges from 0.01 mm to 5 mm, and/or a ratio of an area of the working electrode to an area the reference electrode range from 1 to 1.5.

4. The method of measuring hematocrit as claimed in claim 1, wherein a frequency of each set of square wave voltages ranges from 100 Hz to 4000 Hz, an amplitude of each set of square wave voltages is greater than or equal to 0.01 V, and/or a voltage increment in each set of square wave voltages ranges from 0.01 V to 0.4 V.

5. The method of measuring hematocrit as claimed in claim 1, wherein a voltage sweep range of each set of square wave voltages ranges from 0 V to 0.8 V, and/or a duration of application of each set of square wave voltages ranges from 0.01 seconds to 4 seconds.

6. The method of measuring hematocrit as claimed in claim 1, wherein the sets of square wave voltages are identical to one another, except for application timings.

7. The method of measuring hematocrit as claimed in claim 1, wherein the plurality of feedbacks related to hematocrit are respectively obtained from an electrical reaction in the whole blood sample induced by the plurality of sets of square wave voltages, and the plurality of feedbacks are current values.

* * * * *